(12) United States Patent
Carlberg et al.

(10) Patent No.: US 8,754,246 B2
(45) Date of Patent: Jun. 17, 2014

(54) SEPARATING PHASES OF A MIXTURE

(75) Inventors: Philip J. Carlberg, Lake Jackson, TX (US); Hannah L. Crampton, Lake Jackson, TX (US); Joe J. Longoria, Houston, TX (US)

(73) Assignee: Dow Global Technologies, LLC, Midland, MI (US)

( * ) Notice: Subject to any disclaimer, the term of this patent is extended or adjusted under 35 U.S.C. 154(b) by 0 days.

(21) Appl. No.: 13/983,353

(22) PCT Filed: Feb. 3, 2012

(86) PCT No.: PCT/US2012/023827
§ 371 (c)(1),
(2), (4) Date: Aug. 2, 2013

(87) PCT Pub. No.: WO2012/106630
PCT Pub. Date: Aug. 9, 2012

(65) Prior Publication Data
US 2013/0310583 A1  Nov. 21, 2013

Related U.S. Application Data

(60) Provisional application No. 61/439,730, filed on Feb. 4, 2011.

(51) Int. Cl.
*C07D 301/12* (2006.01)
(52) U.S. Cl.
USPC ........................................... 549/531
(58) Field of Classification Search
USPC ........................................... 549/531
See application file for complete search history.

(56) References Cited

U.S. PATENT DOCUMENTS

| | | | |
|---|---|---|---|
| 4,117,066 A | 9/1978 | Mollet et al. | |
| 4,370,240 A | 1/1983 | Brownell et al. | |
| 5,252,758 A | 10/1993 | Clerici et al. | |
| 5,620,935 A | 4/1997 | Thiele | |
| 5,952,530 A | 9/1999 | Argyropoulos | |
| 6,063,941 A | 5/2000 | Gilbeau | |
| 6,169,050 B1 | 1/2001 | Catinat et al. | |
| 6,288,248 B1 * | 9/2001 | Strebelle et al. | 549/518 |
| 6,350,888 B1 * | 2/2002 | Strebelle et al. | 549/529 |
| 6,818,132 B2 | 11/2004 | Haubs et al. | |

(Continued)

FOREIGN PATENT DOCUMENTS

| | | |
|---|---|---|
| CN | 101747296 | 6/2010 |
| CN | 101747297 | 6/2010 |
| CN | 101279958 | 10/2010 |
| DE | 19962719 | 6/2001 |
| WO | 2008087657 | 7/2008 |
| WO | 2009063487 | 5/2009 |

OTHER PUBLICATIONS

Thiele, G.F. and Roland, E., "Propylene epoxidation with hydrogen peroxide and titanium silicalite catalyst: Activity, deactiviation, and regeneration of the catalyst," Journal of Moelcular Catalysis A: Chemical 117 (1997 351-356.
Clerici, Mario G.; Ingallina; Patrizia. "Epoxidation of lower olefins with hydrogen peroxide and titanium silicalite." Journal of Catalysis, 1993, 140, 71-83.
Zhang, Zhaoguang; Kang, Jingna, Yaquan. "Effects of organic solvent addition on the epoxidation of propene catalyzed by TS-1." Reaction of Kinetics and Catalysis Letters 2007, 92(1), 49-52.
GEA Westfalia Separator; "Separation, Solution, Success"; 2010.

*Primary Examiner* — T. Victor Oh
(74) *Attorney, Agent, or Firm* — Brooks, Cameron & Huebsch, PLLC

(57) ABSTRACT

Embodiments of the present disclosure include a process for separating phases of a mixture including a liquid aqueous phase, a liquid organic phase, and a solid phase and extracting at least an oxirane from the liquid aqueous phase with an extraction solvent.

14 Claims, 3 Drawing Sheets

(56) References Cited

U.S. PATENT DOCUMENTS

| | | |
|---|---|---|
| 7,323,578 B2 | 1/2008 | Catinat et al. |
| 7,705,167 B2 | 4/2010 | Shinohara et al. |
| 7,838,455 B2 | 11/2010 | Kwak et al. |
| 8,534,963 B2 | 9/2013 | Luik |
| 2006/0016760 A1 | 1/2006 | Bozak et al. |
| 2010/0264091 A1 | 10/2010 | Nazzer |
| 2011/0137054 A1 | 6/2011 | Postma et al. |
| 2012/0130095 A1 | 5/2012 | Crampton et al. |

* cited by examiner

SEPARATING PHASES OF A MIXTURE

This application is a National Stage application under 35 U.S.C. 371 of PCT/US2012/023827, filed on Feb. 3, 2012 and published as WO 2012/106630 on Aug. 9, 2012, which claims the benefit of U.S. Provisional Application Ser. No. 61/439,730 filed Feb. 4, 2011, the entire contents of which are incorporated herein by reference in its entirety.

CROSS-REFERENCE TO RELATED APPLICATIONS

This application claims the benefit under 35 U.S.C. §119(e) of U.S. Provisional Patent Application No. 61/439,730, filed Feb. 4, 2011, which is incorporated herein by reference in its entirety.

FIELD OF DISCLOSURE

Embodiments of the present disclosure are directed to a process for separating phases of a mixture; more specifically, embodiments are directed toward separating phases of a mixture produced during a reaction that forms an oxirane.

BACKGROUND

Various products can be produced by reacting one or more reactants in the presence of a catalyst. In some reactions, the catalyst can be a different physical state than the one or more reactants. For example, two liquid reactants can be reacted in the presence of a solid catalyst. As an example of a particular reaction using reactants and catalysts having different physical states, an oxirane can be produced by reacting a liquid olefin and a liquid peroxide compound in the presence of a solid catalyst, where such a reaction may also be referred to as an "epoxidation reaction." Once the reaction is complete, various components of the mixture can be separated to obtain the product (e.g., the oxirane).

SUMMARY

One or more embodiments of the present disclosure include a process for separating phases of a mixture, where the process includes receiving a mixture that includes a liquid aqueous phase, a liquid organic phase containing an oxirane, and a solid phase, wherein the liquid organic phase has a density greater than the liquid aqueous phase, the solid phase has a density greater than the liquid organic phase, and the solid phase has an affinity for the liquid aqueous phase; allowing the mixture to separate into the liquid aqueous phase and the liquid organic phase, wherein a first part of the solid phase remains suspended in the liquid aqueous phase and a second part of the solid phase settles through the liquid organic phase to a density driven position; recovering the liquid aqueous phase including the first part of the solid phase; and extracting at least the oxirane from the liquid aqueous phase with an extraction solvent.

One or more embodiments of the present disclosure also include a process for preparing an oxirane, where the process includes (a) reacting an olefin, wherein the olefin is selected from one of (i) an aliphatic olefin or substituted aliphatic olefin (ii) a cycloaliphatic olefin, (iii) an aromatic olefin, (iv) a cycloaromatic olefin, and (v) mixtures thereof; a solid phase catalyst, a hydrogen peroxide solution, and a solvent mixture with an alcohol and a non-reactive co-solvent to form a reaction mixture; (b) separating an effluent containing the reaction mixture and reaction products into a liquid aqueous phase and a liquid organic phase to separate the solid phase catalyst from the liquid organic phase, wherein an effluent containing the reaction mixture and reaction products have a liquid aqueous phase and a liquid organic phase, wherein the liquid organic phase has a density greater than the liquid aqueous phase, the solid phase catalyst has a density greater than the liquid organic phase, and the solid phase catalyst has an affinity for the liquid aqueous phase, and wherein a first part of the solid phase catalyst remains suspended in the liquid aqueous phase and a second portion of the solid phase catalyst settles through the liquid organic phase to a density driven position; (c) recovering, in at least one operation unit, the liquid organic phase of step (b) including the non-reactive co-solvent, the olefin, and the oxirane; (d) recovering, in at least one operation unit, the liquid aqueous phase of step (b) including the first part of the solid phase catalyst; and (e) extracting, in at least one separation unit operation, the olefin and oxirane present in the liquid aqueous phase of step (d) from the liquid aqueous phase with an extraction solvent.

The above summary of the present disclosure is not intended to describe each disclosed embodiment or every implementation of the present disclosure. The description that follows more particularly exemplifies illustrative embodiments. In several places throughout the application, guidance is provided through lists of examples, where examples can be used in various combinations. In each instance, the recited list serves only as a representative group and should not be interpreted as an exclusive list.

DEFINITIONS

Figure 1:
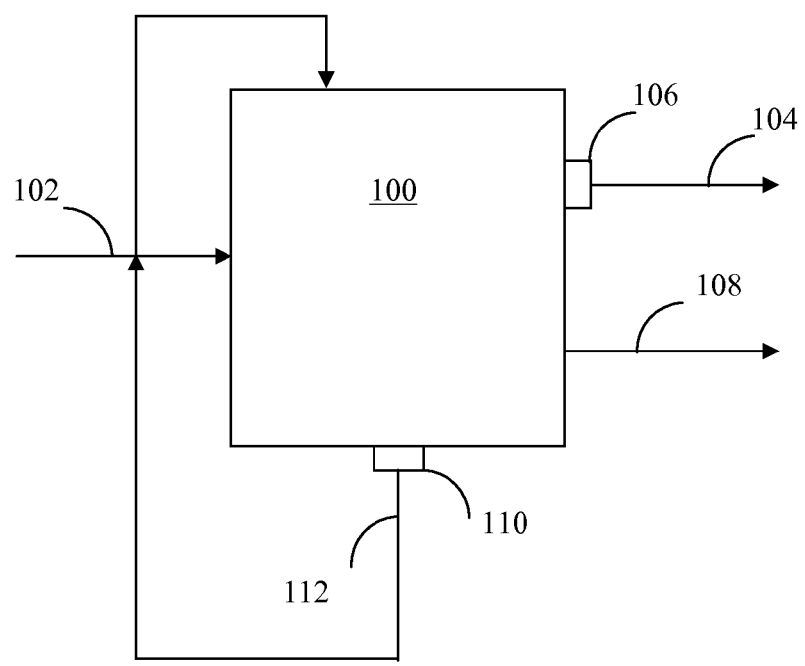
FIG. 1 illustrates a vessel used in a process according to an embodiment of the present disclosure.

"Oxirane" refers to a compound in which an oxygen atom is directly attached to two adjacent or non-adjacent carbon atoms of a carbon chain or ring system. Epichlorohydrin, which is formed from an epoxidation reaction of allyl chloride, is an example of an oxirane.

"Slurry" refers to a suspension of a solid (e.g., solid phase) in a liquid (e.g., liquid aqueous phase).

The term "and/or" means one, one or more, or all of the listed elements.

Unless otherwise indicated, all numbers expressing quantities of components, weight parts, temperatures, percentages, and so forth used in the specification and claims can be understood as being modified by the term "about."

As used herein, "a" "an" "the" "at least one" and "one or more" are used interchangeably. The terms "includes" and "comprises" and variations thereof do not have a limiting meaning where these terms appear in the description and claims. Thus, for example, a solvent mixture with an alcohol and a non-reactive co-solvent can be interpreted to mean that the solvent mixture includes one or more alcohol(s) and one or more non-reactive co-solvent(s).

Also herein, the recitations of numerical ranges by endpoints include all numbers subsumed with that range (e.g. 1 to 5 includes 1, 1.5, 2, 2.75, 3, 3.8, 4, 5, etc.).

A "peroxide compound" refers to a compound containing one or more peroxide (—O—O—) functionalities, including organic or inorganic peroxides, peroxide adducts, or peracids.

DETAILED DESCRIPTION

Embodiments of the present disclosure provide a process for separating phases of a mixture. The process may include receiving a mixture including a liquid aqueous phase, a liquid organic phase including an oxirane, and a solid phase. The liquid organic phase can have a density greater than the liquid aqueous phase and the solid phase can have a density greater than the liquid organic phase. For one or more embodiments, the solid phase can have an affinity for the liquid aqueous phase. The affinity of the solid phase for the liquid aqueous phase can allow a first part of the solid phase to remain suspended in the liquid aqueous phase.

Previous approaches for separating mixtures having components with different physical states (e.g., liquid and solid) include using centrifugation to separate the different physical states. In centrifugation, the more-dense components of the mixture migrate away from an axis of the centrifuge, while less-dense components of the mixture migrate towards the axis. However, using mechanical separation techniques such as centrifugation can increase the cost of separation.

Surprisingly, it has been found that a solid phase according to the present disclosure has an affinity for a liquid aqueous phase and can remain in the liquid aqueous phase even when the liquid aqueous phase has a density lighter than the liquid organic phase and the solid phase has a density greater than both the liquid aqueous phase and the liquid organic phase. This affinity of the solid phase for the liquid aqueous phase can allow for non-mechanical separation techniques of the mixture (e.g., gravity decantation).

In the following detailed description of the present disclosure, reference is made to an accompanying drawing that forms a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, chemical and/or structural changes may be made without departing from the scope of the present disclosure.

The figures herein follow a numbering convention in which the first digit or digits corresponds to the drawing figure number and the remaining digits identify an element in the drawing. Similar elements between different figures may be identified by the use of similar digits. For example, 106 may reference element "06" in FIG. 1, and a similar element may be referenced as 206 in FIG. 2. The proportion and the relative scale of the elements provided in the figures are intended to illustrate various embodiments of the present invention and are not to be used in a limiting sense.

For one or more embodiments, the process includes receiving a mixture including a liquid aqueous phase, a liquid organic phase including an oxirane, and a solid phase. For one or more embodiments, the mixture can be an effluent including a reaction mixture of an olefin, a peroxide compound, a solid phase, and a solvent mixture with an alcohol and a non-reactive co-solvent, and reaction products of the reaction mixture, where the reaction products include an oxirane.

For one or more embodiments, the olefin is allyl chloride. For the reaction mixture other olefins besides allyl chloride, or in addition to allyl chloride, can be used. For example, the olefin can be selected from the group consisting of, but not limited to, linear and/or branched acyclic or cyclic aliphatic or aromatic olefins, including those which may contain multiple double bonds. Additional examples of the olefin include, but are not limited to, chloride-butadiene and other linear dialkenes, cyclohexene and other cyclic alkenes and dialkenes, substitute alkenes, such as halogenated alkenes, styrene, divinylbenzene, dicyclopentadiene, other aromatic alkenes and mixtures thereof. Moreover, butenes, pentenes, hexenes, octenes, heptenes, 1-tridecene, mesityl oxide, isoprene, cyclo-octane, cyclohexene or bicyclic compounds such as norbornenes or pinenes may also be used.

For the embodiments, the olefin can be used in a range of from 10 weight percent (wt %) to 90 wt %, preferably 20 wt % to 80 wt %, more preferably 30 wt % to 70 wt %, and still more preferably 40 wt % to 65 wt %, based on a total weight of the total composition which includes all of the components fed to the reaction vessel to form the reaction mixture including for example the weight of all of the liquid components and the solid phase (e.g., catalyst) together herein "the total composition."

For one or more embodiments, the peroxide compound is a hydrogen peroxide solution. For example, the peroxide compound can include, for example, but are not limited to, hydrogen peroxide, urea-hydrogen peroxide adduct, peracetic acid and mixtures thereof. Additional examples of peroxide compounds may include tert-butyl hydroperoxide and ethylbenzene hydroperoxide.

For the embodiments, the peroxide compound can be used in a range of from 1 wt % to 35 wt %, preferably 1 wt % to 20 wt %, more preferably 1 wt % to 10 wt %, and still more preferably 1 wt % to 7 wt %, based on the weight of the total composition.

A variety of peroxide compounds can be used in forming the reaction mixture of the present disclosure. Examples of the peroxide compounds useful in the present disclosure may include, but are not limited to, organic and/or inorganic hydroperoxides, such as hydrogen peroxide, tert-butyl hydroperoxide, ethylbenzene hydroperoxide, acetyl peroxide, benzoyl peroxide, methyl ethyl ketone peroxide, cumene peroxide and combinations thereof. In the present disclosure, preference is given to using hydrogen peroxide as the peroxide compound. The present disclosure as described herein, therefore, also provides a process for using hydrogen peroxide as the peroxide compound. Here, preference is given to using an aqueous hydrogen peroxide.

In one preferred embodiment of the present disclosure, an aqueous solution of hydrogen peroxide at about 30 wt % may be used such that the total amount of molecular hydrogen peroxide may be from about 1 wt % to about 7 wt %, based on the weight of the total composition.

As discussed herein, the solid phase in the mixture can be the catalyst used in the epoxidation reaction between the olefin and the peroxide compound. The catalyst can be selected from, but is not limited to, heterogenized forms of soluble metal catalysts such as ligand-bound rhenium, tungsten, and manganese, as well as solid silicate catalysts that preferably contain titanium. These solid phase catalysts may have the crystal structure of ZSM-5, MCM-22, MCM-41, beta-zeolites, or amorphous titanium on silica.

The catalyst used in the epoxidation reaction can be selected from heterogeneous catalysts which comprise a porous oxide material such as zeolite. As appreciated, zeolites are solid containing silicas which have microporous crystalline ordered channels with a cage structure and pore openings. Along with microporous zeolites, mesoporous and macroporous zeolite type catalysts can also be used. For the embodiments, the catalyst is preferably selected from titanium-silicalites generally known as TS-1 having a MFI structure. It is also possible to use titanium-silicalites with a MEL or intermediate MFI/MEL structure and titanium-silicalites from beta zeolites containing titanium and having a BEA structure. Other titanium containing zeolite catalysts generally known as TS-2, TS-3, ZSM-48 and ZMS-12 can also be used. For the embodiments, a portion or all of the titanium in the zeolite catalyst can be replaced by, but not limited to, boron, aluminum, iron, gallium, vanadium, zirconium, chromium, niobium or a mixture of two or more thereof. Additional examples of zeolites containing titanium, vanadium, chromium, niobium, and zirconium include, but are not limited to, BEA, MOR, TON, MTW, FER, CHA, ERI, RHO, GIS, BOG, NON, EMT, HEU, KFI, FAU, DDR, MTT, RUT, RTH, LTL, MAX, GME, NES, OFF, SGT, EUO, MFS, MWW and ITQ-4. It is also possible to use titanium-containing zeolites having the UTD-1, CIT-1 or CIT-5 structure in the process of the present invention.

For the embodiments, the catalyst can be used within a range of from 0.1 wt % to 30 wt %, more preferably within a range of from 0.1 wt % to 15 wt %, and still more preferably within a range of from 0.1 wt % to 5 wt %, based on the weight of the total composition.

As discussed herein, the solid phase can have an affinity for the liquid aqueous phase. As used herein, "affinity", or "chemical affinity", refers to an attraction or force by which dissimilar chemical species (e.g., the solid phase and liquid aqueous phase) have a tendency to associate with one another. In one or more embodiments the affinity for the solid phase for the liquid aqueous phase is due to van der Waals forces, hydrogen bonding, ionic interactions, and combinations thereof.

For one or more embodiments, the solid phase can include a polar group, a charged group, or a combination thereof to provide the affinity of the solid phase for the liquid aqueous phase. The polar group can include, but is not limited to, a hydroxyl group (—OH), an amine group (—NR$_2$), phosphorous, sulfur, boron, and combinations thereof. The charged group can include, but is not limited to, oxygen ion (O$^-$), nitrogen ion (N$^-$), metal ions, and combinations thereof.

As discussed herein, the mixture can include the solvent mixture with the alcohol. Examples of alcohols may include, but are not limited to, lower alcohols such as alcohols having less than 6 carbon atoms. Examples include, but are not limited to, methanol, ethanol, propanols such as isopropanol, butanols such as tert-butanol, pentanols, and a combination of two or more of these alcohols; halogenated alcohols; and mixtures thereof. For one embodiment, the alcohol in the solvent mixture is methanol.

For the embodiments, the alcohol can be used within a range of from 3 wt % to 40 wt %, preferably within a range of from 3 wt % to 20 wt %, more preferably within a range of from 3 wt % to 10 wt %, and still more preferably within a range of from 3 wt % to 7 wt %, based on the weight of the total composition.

As discussed herein, the solvent mixture can include the non-reactive co-solvent. The non-reactive co-solvent can include a compound which is inert to the epoxidation reaction. For example, the non-reactive co-solvent does not take part in the reaction under the reaction conditions, does not react appreciably with the peroxide compound or the oxirane under reaction conditions, is minimally soluble in water, and has a boiling point substantially different than the oxirane to be produced from the epoxidation reaction.

Examples of the non-reactive co-solvent can include, but are not limited to, aliphatic, cycloaliphatic, and aromatic hydrocarbons; amides (e.g., dimethylformamide, dimethylacetamide, and N-methylpyrrolidone); sulfoxides; certain ketones; diols or polyols, preferably those having less than 6 carbon atoms; and alcohols other than or different from the alcohol mixture. Additionally, the non-reactive co-solvent can include, but is not limited to, linear and cyclic alkanes of $C_3$-$C_{18}$, halogenated hydrocarbons, deactivated aromatics, and solvents containing nitriles (e.g., acetonitrile); or mixtures thereof. For example, the non-reactive co-solvent may include, but is not limited to, carbon tetrachloride, propyl chloride, chloroform, dichloromethane, dichloroethane, hexane, octane, decalin, perfluorodecalin, mono- or poly-chlorinated benzenes, mono- or poly-brominated benzenes, acetophenone, benzonitrile, acetonitrile, trichlorotrifluoroethane, trichloroethanol, trifluoroethanol, tricresyl phosphate, or mixtures of two or more of the above-mentioned compounds. For one or more embodiments, the non-reactive co-solvent is 1,2-dichlorobenzene.

For the embodiments, the non-reactive co-solvent can be used in a range of from 5 wt % to 70 wt %, preferably within a range of from 5 wt % to 55 wt %, more preferably within a range of from 10 wt % to 40 wt %, and still more preferably within a range of from 10 wt % to 30 wt %, based on the weight of the total composition.

In a preferred embodiment of the present disclosure, 1,2-dichlorobenzene may be advantageously used as the non-reacting co-solvent in concentrations between about 10 wt % to about 30 wt %, based on the weight of the total composition.

For one or more embodiments, other optional components, that may be useful in the present disclosure, may be used in the process of the present disclosure. For example, the optional components may comprise compounds that can be added to the composition to enhance the reaction rate, the selectivity of the reaction, and/or the catalyst lifetime. The preferred optional components and their relative concentrations useful in the composition of the present disclosure can be determined by the skilled artisan.

For one or more embodiments, the process includes allowing the mixture to separate into the liquid aqueous phase and the liquid organic phase. The liquid aqueous phase and the liquid organic phase can be two immiscible liquids that form an immiscible fluid interface. Allowing the mixture to separate into the liquid aqueous phase and the liquid organic phase can include allowing the mixture to settle in a vessel. The liquid organic phase can have a density greater than the liquid aqueous phase. As such, the liquid organic phase settles below the liquid aqueous phase, which has a density that is less than the liquid organic phase. In other words, the liquid organic phase is a bottom layer in the vessel and the liquid aqueous phase is a top layer in the vessel.

As discussed herein, the mixture can be the effluent from the epoxidation reaction including the reaction mixture and the reaction products. The reaction mixture can include the olefin, peroxide compound, oxirane, the solid phase, and the solvent mixture with the alcohol and the non-reactive co-solvent. The reaction products include the oxirane such as epichlorohydrin. For one or more embodiments, allowing the mixture to settle in the vessel can include agitating the mixture. Agitating the mixture can assist in separating the solid phase from the liquid organic phase. Agitation can be performed by known means for agitating, such as, but not limited to, stirring with an agitator or by inducing shear with a mixing element in the vessel. For the embodiments, the agitation is performed such that the immiscible fluid interface between the liquid aqueous phase and the liquid organic phase is maintained within the vessel.

For one or more embodiments, a first part of the solid phase remains suspended in the liquid aqueous phase in the vessel. The first part of the solid phase can remain suspended in the liquid aqueous phase because of the affinity of the solid phase for the liquid aqueous phase. For one or more embodiments, the first part of the solid phase is greater than 50 wt %, preferably greater than 75 wt %, more preferably greater than 95 wt %, and still more preferably greater than 98 wt %, based on a total weight of the solid phase.

For one or more embodiments a second part of the solid phase can settle through the liquid organic phase to a density driven position. While the solid phase has an affinity for the liquid aqueous phase, an amount of the solid phase will not remain suspended in the liquid aqueous phase because its surface has been modified. As discussed herein, the solid phase has a density greater than both the liquid aqueous phase and the liquid organic phase. Therefore, the second part of the solid phase that does not remain suspended in the liquid aqueous phase can settle at least partially through the liquid organic phase to a density driven position. For one or more embodiments, the second part of the solid phase is less than 50 wt %, preferably less than 25 wt %, more preferably less than 5 wt %, and still more preferably less than 2 wt %, based on a total weight of the solid phase.

For one or more embodiments, the process includes recovering the liquid organic phase. Recovering the liquid organic phase can include removing the liquid organic phase from a point within a volume of the liquid organic phase in the vessel. For one or more embodiments, the liquid organic phase recovered from the vessel can contain less than 1 wt % of the solid phase. In one embodiment, the liquid organic phase contains zero (0) wt % of the solid phase. For one or more embodiments, recovering the liquid organic phase from the vessel can be performed by known techniques for removing a liquid from a vessel. Examples can include, but are not limited to, an outlet port, an overflow port, a pressure differential, pumping with a pump capable of handling a solid slurry, and combinations thereof.

The liquid organic phase removed from the vessel can include dissolved water, the second part of the solid phase, oxirane, olefin, and the solvent mixture with the alcohol and non-reactive co-solvent. The liquid organic phase removed from the vessel can contain a majority of the oxirane formed during the epoxidation reaction (e.g., more than 50 wt %, based on a total weight of the oxirane produced). The liquid organic phase removed from the vessel can undergo further processing to recover the oxirane and separate and recycle the olefin, the solvent mixture with the alcohol and the non-reactive co-solvent.

For one or more embodiments, the process includes recovering the liquid aqueous phase that includes the first part of the solid phase. Recovering the liquid organic phase from the vessel can be performed by known techniques for removing a liquid from a vessel. Examples can include, but are not limited to, an outlet port, an overflow port, a pressure differential, pumping with a pump capable of handling a solid slurry, and combinations thereof. In one embodiment, the liquid aqueous phase is removed from a liquid aqueous phase overflow port of the vessel. The liquid aqueous phase can include the first part of the solid phase, water, peroxide compound, oxirane, olefin, the solvent mixture with the alcohol and the non-reactive co-solvent. The liquid aqueous phase includes a majority of water along with the peroxide compound and the alcohol of the solvent mixture present in the reaction mixture. However, the liquid aqueous phase can include a portion of the oxirane and the olefin. For one embodiment, the oxirane and the olefin can be less than 5 wt %, based on the total weight of the liquid aqueous phase.

For one or more embodiments, the process includes extracting at least the oxirane from the liquid aqueous phase with an extraction solvent. For one or more embodiments, the process can further include extracting the olefin from the liquid aqueous phase with the extraction solvent. For the present disclosure, extracting the oxirane and the olefin can prevent destruction of the oxirane and the olefin present in the liquid aqueous phase. For example, the liquid aqueous phase could be sent to a digest reactor to deplete the peroxide compound to acceptable levels before the liquid aqueous phase is sent to a distillation unit operation. However, if the oxirane and olefin are not extracted from the liquid aqueous phase prior to the digest reactor, the oxirane and olefin can be destroyed during the digestion of the peroxide compound and during distillation operations.

Eliminating the oxirane can decrease the profitability of the process since the portion of the product is being eliminated versus being sold. Additionally, eliminating the olefin that has not reacted with the peroxide compound during the epoxidation reaction can increase the cost of producing the oxirane since the olefin is not reacting to form the oxirane. Thus, extracting the oxirane from the liquid aqueous phase can help increase the efficiency of the epoxidation reaction since more of the oxirane will be recovered. Moreover, extracting the olefin can reduce costs associated with producing the oxirane by not eliminating starting materials and thereby minimizing the amount of olefin used to produce the oxirane.

For one or more embodiments, the liquid aqueous phase can be separated from the first part of the solid phase before the oxirane and olefin are extracted using the extraction solvent. Separating the first part of the solid phase from the liquid aqueous phase can be performed by known separation techniques including, but not limited to, hydrocyclone, filtration, centrifugation, and gravity. Alternatively, the oxirane and olefin can be extracted from the liquid aqueous phase without having to separate the liquid aqueous phase from the first part of the solid phase.

For one or more embodiments, the extraction solvent can be selected from solvents that are present in the process for producing the oxirane. In one embodiment, the extraction solvent is different than the olefin used in the process for producing the oxirane. In one embodiment, the extraction solvent is 1,2-dichlorobenzene. Additionally, the extraction solvent used does not increase an amount of the olefin in the liquid aqueous phase. Additional extraction solvents can include, but are not limited to, acetophenone, isopropyl chloride, n-propyl chloride, tricresyl phosphate, and trichloropropane.

For one or more embodiments, extracting the oxirane and olefin is done from only the liquid aqueous phase. Extracting the oxirane and olefin from only the liquid aqueous phase can reduce an amount of extraction solvent used as compared to an amount of extraction solvent that would be used to extract the oxirane and olefin from both the liquid aqueous phase and the liquid organic phase. Reducing the amount of the extraction solvent used can lower a unit ratio of extraction solvent needed for the production of the oxirane. That is, extracting from only the liquid aqueous phase reduces the amount of extraction solvent used for producing the same amount of oxirane as a process that extracts from both the liquid aqueous and liquid organic phase. Additionally, the reduced amount of extraction solvent is such that, unlike previous approaches, it is not cost or energy prohibitive to send the extraction solvent to distillation, rather than to the reactor; consequently, increasing the efficiency and production of the process.

The process of the present disclosure does not require the olefin in the liquid aqueous phase to be recovered or destroyed. For example, using an extraction solvent that is used in the epoxidation reaction allows for the extraction solvent that has been used to extract the olefin from the liquid aqueous phase to be recycled to a reactor of the epoxidation reaction. This helps to minimize the throughput of the extraction solvent, which can decrease the cost of solvent recovery operations. For example, increasing the throughput of extraction solvent can increase the solvent recovery costs since the extraction solvent would be distilled prior to recycling to a reactor.

For one or more of the embodiments, the reaction mixture can include other optional compounds that may be useful in the present disclosure. For example, optional compounds that can enhance a reaction rate, a selectivity of the epoxidation reaction, and/or the solid phase catalyst lifetime can be included. Examples of optional compounds can include, but are not limited to, acids, bases, metal ions, and combinations thereof.

As discussed herein, embodiments of the present disclosure provide a process for preparing an oxirane. The process can include (a) reacting the olefin, wherein the olefin is selected from one of (i) an aliphatic olefin or substituted aliphatic olefin (ii) a cycloaliphatic olefin, (iii) an aromatic olefin, (iv) a cycloaromatic olefin, and (v) mixtures thereof; the solid phase catalyst, the hydrogen peroxide solution, the solvent mixture with the alcohol and the non-reactive co-solvent to form the reaction mixture.

For one or more embodiments, the process can include (b) separating the effluent containing the reaction mixture and reaction products into the liquid aqueous phase and the liquid organic phase to separate the solid phase catalyst from the liquid organic phase. As discussed herein, the liquid organic phase can have a density greater than the liquid aqueous phase and the solid phase catalyst can have a density greater than the liquid organic phase. Additionally, the solid phase catalyst can have an affinity for the liquid aqueous phase. The liquid organic phase can settles beneath the liquid aqueous phase due to the density difference. However, the solid phase catalyst remains with and suspended within the liquid aqueous phase (e.g., the upper layer) irrespective of the density difference because of the affinity of the solid phase catalyst for the liquid aqueous phase. The liquid aqueous phase includes the first part of the solid phase and the liquid organic phase can include the second portion of the solid phase catalyst that has settled through the liquid organic phase to the density driven position.

For one or more embodiments, the process can include (c) recovering, in at least one operation unit, the liquid organic phase of step (b) including the non-reactive co-solvent, the olefin, and the oxirane, as discussed herein.

For one or more embodiments, the process can include (d) recovering, in at least one operation unit, the liquid aqueous phase of step (b) including the first part of the solid phase catalyst, and (e) extracting, in at least one separation unit operation, organic compounds present in the liquid aqueous phase of step (d) from the liquid aqueous phase with an extraction solvent. For one or more embodiments, the organic compounds include the oxirane and the olefin. The extraction solvent can be selected from the extraction solvents as discussed herein.

For one or more embodiments of the present disclosure, the process can further include (f) separating the oxirane from the liquid organic phase, (g) recovering the oxirane product from step (f), and (h) recycling a remaining amount of the olefin and the solvent mixture with the alcohol and the non-reactive co-solvent stream of step (g) to the reaction mixture.

FIG. 1 illustrates a vessel used in a process according to an embodiment of the present disclosure. FIG. 1 illustrates a vessel 100 according to an embodiment of the present disclosure. Stream 102 is the mixture including the liquid aqueous phase, the liquid organic phase, and the solid phase. The vessel 100 can receive stream 102 from a reaction vessel (see FIG. 3).

As discussed herein, the mixture can be the effluent including the reaction mixture and the reaction products from the epoxidation. For example, stream 102 can be the effluent from the epoxidation reaction and include the oxirane, olefin, peroxide compound, solid phase catalyst, the solvent mixture with the alcohol and the non-reactive co-solvent, and the oxirane. For one or more embodiments, the vessel 100 can also be used as the reaction vessel to form the oxirane.

For one or more embodiments, the mixture (i.e., the effluent) is allowed to separate in vessel 100. For example, the liquid aqueous phase can separate from the liquid organic phase and the solid phase can be suspended within the liquid aqueous phase. As discussed herein, the liquid aqueous phase can include the first part of the solid phase catalyst and the liquid organic phase can include the second part of the solid phase catalyst that settles through the liquid organic phase to the density driven position. The vessel 100 may be selected from known separation vessels, including, but not limited to, decanters, hydrocyclones, mechanically driven high gravity devices, or other separation apparatus known in the art. In one embodiment, the vessel 100 is a gravity decanter.

For one or more embodiments, stream 104 contains the liquid aqueous phase including the first part of the solid phase. The liquid aqueous phase can be removed from the vessel 100 by allowing the liquid aqueous phase to overflow from a liquid aqueous phase overflow port 106 of vessel 100. The contents of stream 104 can include the first part of the solid phase catalyst, water, peroxide compound, olefin, oxirane, and the alcohol of the solvent mixture. Stream 104 can be transported to further processes and/or unit operations, as discussed herein.

Stream 108 contains the liquid organic phase including the second part of the solid phase. The contents of stream 108 can include the second part of the solid phase catalyst, oxirane, olefin, and the solvent mixture with the alcohol the non-reactive co-solvent. Stream 108 can be transported to further processes and/or unit operations. For example, stream 108 can be filtered to remove the second part of the solid phase from the liquid organic phase or sent to distillation towers to recover the oxirane and separate and recycle other compounds of the liquid organic phase (e.g., the olefin), the solvent mixture with the alcohol and the non-reactive co-solvent.

For one or more embodiments, vessel 100 can have a drain valve 110 to periodically drain a portion of the liquid organic phase to remove at least a portion of the second part of the solid phase that has settled to a density driven position. Stream 112 includes the drained liquid organic phase that contains the second part of the solid phase. For one or more embodiments, stream 112 can be filtered to separate the solid catalyst phase from the liquid organic phase.

In one or more embodiments, stream 112 can be recycled back to stream 102. Additionally, stream 112 can be recycled back to the vessel 100. As seen in FIG. 1, stream 112 can be connected to stream 102 and/or the vessel 100 such that a portion of stream 112 can be recycled to stream 102 and/or a portion can of stream 112 can be recycled to the vessel 100. Recycling stream 112 to stream 102 allows the liquid organic phase drained from vessel 100 to repeat the separation process. In one or more embodiments, a portion of stream 112 does not get recycled and can be transported to further processes and/or unit operations.

Figure 2:
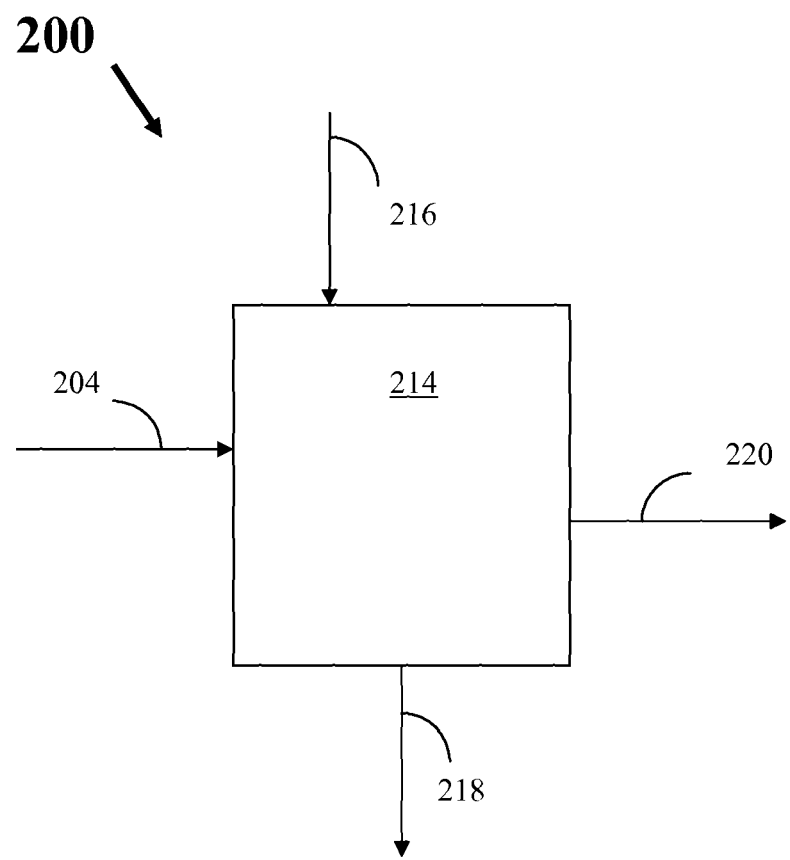
FIG. 2 illustrates an extraction vessel used in a process according to an embodiment of the present disclosure.

FIG. 2 illustrates an extraction vessel 214 used in the process according to an embodiment of the present disclosure.

The extraction vessel 214 can include an extraction unit operation in which a suitable extraction solvent or mixture of extraction solvents, introduced in stream 216, can be mixed with stream 204. As discussed herein, stream 204 can be filtered prior to entering the extraction vessel 214 to remove the first portion of the solid phase catalyst from the liquid aqueous phase.

Stream 216 can include one or more extraction solvents, as discussed herein. Stream 204 can be mixed with stream 216 in the extraction vessel 214 to extract the oxirane and the olefin from the other components of the liquid aqueous phase. For example, the oxirane and the olefin can be extracted from the other components including, the peroxide compound, water, and the alcohol of the solvent mixture. As seen in FIG. 2, stream 220 can remove the other components such as the peroxide compound, water, and the alcohol from the extraction vessel 214. Stream 220 can be sent to storage, or for further processing such as purification and disposal. For example, stream 220 can be sent to the digest reactor (not shown), where the peroxide compound is digested to acceptable limits prior to disposal.

Stream 218 can include the extraction solvent plus the oxirane and the olefin. For one or more embodiments, stream 218 can be recycled back to the reaction vessel (see FIG. 3) to allow the olefin to react in the epoxidation reaction and to recirculate the oxirane. As discussed herein, extracting the oxirane and the olefin from the liquid aqueous phase can reduce an amount of starting materials (e.g., the olefin) and reaction products (e.g., the oxirane) that are disposed of during the process for producing the oxirane.

Figure 3:
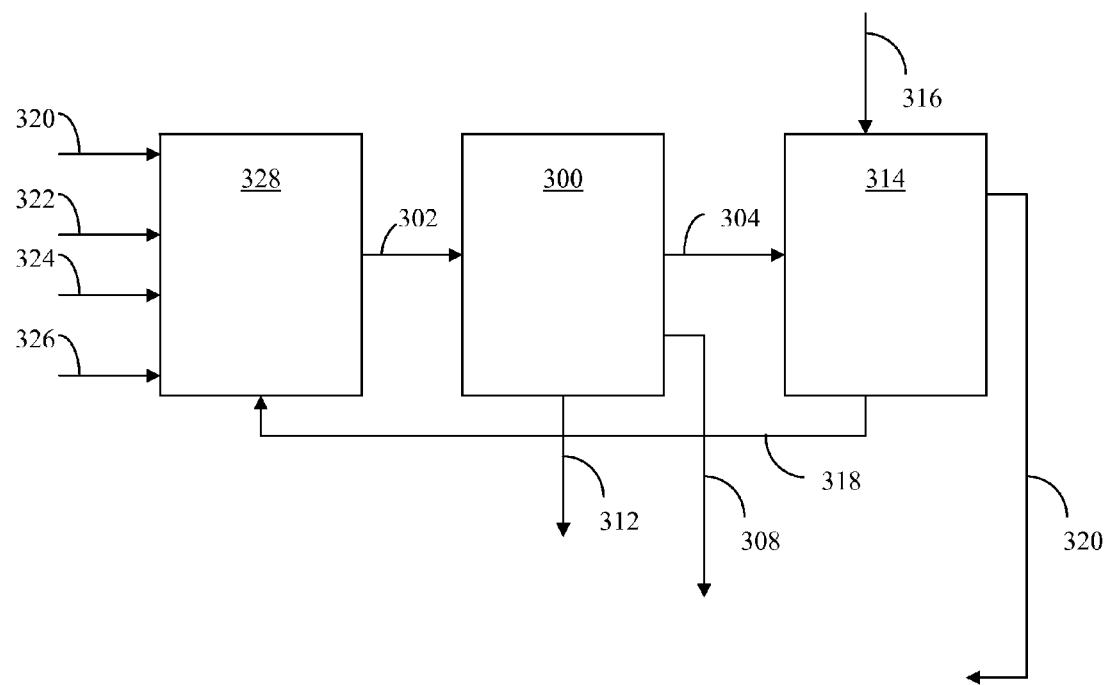
FIG. 3 illustrates a combination of vessels used in a process according to an embodiment of the present disclosure.

FIG. 3 illustrates a combination of vessels used in a process according to an embodiment of the present disclosure. For one or more embodiments, streams 320, 322, 324, and 326 can be fed to a reaction vessel 328 to form the reaction mixture. The reaction vessel 328 can be selected from one or more continuous stirred tank reactors (CSTRs), tubular reactors, fixed-bed reactors, or combinations thereof.

Stream 320 can include the olefin, such as an allyl chloride feed stream. Stream 322 can include the peroxide compound, such as a hydrogen peroxide solution. Stream 324 can include a single or mixed alcohols feed stream. Additionally, stream 326 can include the non-reactive co-solvent. For one or more embodiments, the reaction vessel 328 includes the solid phase catalyst such as a TS-1 catalyst.

For one or more embodiments, streams 320, 322, 324, and 326 can be introduced into the reaction vessel 328 either separately or together. Additionally, streams 320, 322, 324, and 326 may be combined together into one feed stream prior to being introduced into the reaction vessel 328. Streams 320, 322, 324, and 326 may be introduced at a single point or at multiple points of the reaction vessel 328. The relative amounts of streams 320, 322, 324, and 326 are chosen such that when they are combined in the reaction vessel 328 a separate liquid aqueous phase exists along with one or more liquid organic phases, the solid phase catalyst phase, and optionally a vapor phase above the reaction mixture.

For one or more embodiments, the vessel 300 can receive the effluent in stream 302. Stream 302 can include the liquid aqueous phase, the liquid organic phase, and the solid phase catalyst. Vessel 300 can be selected from a number of separation vessels, as discussed herein with respect to FIG. 1. In one embodiment, vessel 300 is a gravity decanter. Stream 308 including the liquid organic phase may be removed from vessel 300 and can be sent for further processing, as discussed herein. Additionally, stream 312, including the drained liquid organic phase and the solid phase catalyst, can be recycled back to stream 302 or to the vessel 300, as discussed in reference to FIG. 1.

As seen in FIG. 3, the extraction vessel 314 can receive stream 320 from vessel 300. As discussed herein, the extraction vessel 314 can include the extraction unit operation in which the extraction solvent or mixture of extraction solvents as stream 316 is mixed with stream 304. Stream 318 including the extraction solvent plus the oxirane and olefin can be recycled back to the reaction vessel 328, as discussed herein with reference to FIG. 2. Additionally, stream 320 can proceed to further processing, as discussed herein.

EXAMPLES

The following examples further illustrate the present disclosure in detail, but are not to be construed to limit the scope of the disclosure.

Materials

Catalyst, titanium silicate zeolite (TS-1), available from Süd-Chemie.

Olefin, allyl chloride (99.4% purity), obtained from The Dow Chemical Company.

Peroxide compound, hydrogen peroxide (30 wt %/aq), available from Sigma Aldrich.

Alcohol, Methanol, available from Sigma Aldrich.

Oxirane, epichlorohydrin, available from Sigma Aldrich.

Non-reactive co-solvent 1,2-dichlorobenzene, available from Sigma Aldrich.

All materials were used as-is without further purification or modification.

Test Methods

Gas Chromatography (GC)

The amounts of the organic compounds remaining in samples were determined using a Hewlett Packard 6890 series G1530A gas chromatography with a Hewlett Packard 7682 series injector and flame ionization detector.

Hydrogen Peroxide Titration

Peroxide amounts were analyzed by iodometric titration using 0.01N sodium thiosulfate. The peroxide concentration may be calculated as follows: ppm $H_2O_2$=(mL titrant used)(0.01 N)(17000)/g sample. Titrations were performed using a Mettler Toledo DL5x V2.3 titrator with a DM140 sensor.

Example 1

Separating Phases of a Reaction Mixture

Example 1 illustrates an embodiment of the process of the present disclosure. Example 1 illustrates a continuous operation separating the liquid aqueous phase and the liquid organic phase in a gravity decanter, where the first portion of the solid phase catalyst remains in the liquid aqueous phase.

Example 1

A reaction mixture including the reaction products of an epoxidation reaction had the following composition: TS-1 catalyst (1 wt %), water (15.2 wt %), hydrogen peroxide (3.1 wt %), epichlorohydrin (8.6 wt %), allyl chloride (30.1 wt %), methanol (4.3 wt %), and 1,2-dichlorobenzene (37.7 wt %), where the wt % is based on a total weight of the reaction mixture including the reaction products. The reaction mixture was received in a 1-liter jacketed glass separatory funnel at a rate of 23 gram/minute (g/min).

The reaction mixture, in the separatory funnel, was cooled and maintained at a temperature of 35° C. using a glycolwater mixture circulating through the separatory funnel jacket. The reaction mixture is allowed to settle in the separatory funnel and separate into a liquid aqueous phase containing the TS-1 catalyst and a liquid organic phase.

The liquid organic phase is pumped form the separatory funnel at a rate of 17.8 gram/minute (g/min). The liquid aqueous phase has and a rate of overflow from the separatory funnel of 5.2 gram/minute (g/min).

The resulting composition of the liquid aqueous phase, as analyzed by gas chromatography, is shown in Table I. The resulting composition of the liquid organic phase as analyzed by gas chromatography is shown in Table II. The wt % of the components in Table I and Table II is based on a total weight of the liquid organic phase, excluding the TS-1 catalyst. The wt % of the TS-1 catalyst is based on gravimetric analysis, dry weight basis.

TABLE I

| Liquid Aqueous Phase | Wt % |
| --- | --- |
| TS-1 Catalyst | 4.2 |
| Water | 67.6 |
| Hydrogen Peroxide | 13.6 |
| Epichlorohydrin | 1.5 |
| Allyl Chloride | 0.4 |
| Methanol | 16.9 |

TABLE II

| Liquid Organic Phase | Wt % |
| --- | --- |
| TS-1 Catalyst | 0.0 |
| Water | 0.2 |
| Epichlorohydrin | 10.8 |
| Allyl Chloride | 39.2 |
| Methanol | 0.6 |
| 1,2-dichlorobenzene | 49.2 |

As seen in Table I, a first part (4.2 wt %) of the TS-1 catalyst remained suspended with the liquid aqueous phase. This represents 95% of the total catalyst fed to the separatory funnel.

As seen in Table II, the removed liquid organic phase did not contain the TS-1 catalyst. However, a second part (approximately 5 wt % of the total catalyst fed to the separatory funnel, not shown in Table I or Table II) of the TS-1 catalyst fell out of the liquid aqueous phase and settled through the liquid organic phase to a density driven position. The second part of the TS-1 catalyst was removed separately from the separatory funnel via a drain valve.

Examples 2-15e

Extracting the Oxirane and Olefin from the Liquid Aqueous Phase

A liquid aqueous phase, whose composition is shown in Table III, is used as a representative liquid aqueous phase that would be generated during a process to make epichlorohydrin utilizing allyl chloride and hydrogen peroxide. Examples 2-15e illustrate the extraction of the oxirane and the olefin from the liquid aqueous phase.

Example 2

Liquid aqueous phase, as described above, and whose composition is shown in Table III (9.0258 g) was added to a 20-mL sample vial. 1,2-Dichlorobenzene (1.0097 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 3

Liquid aqueous phase, as described above, and whose composition is shown in Table III (7.0071 g) was added to a 20-mL sample vial. 1,2-Dichlorobenzene (3.0072 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 4

Liquid aqueous phase, as described above, and whose composition is shown in Table III (5.0257 g) was added to a 20-mL sample vial. 1,2-Dichlorobenzene (5.0179 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 5

Liquid aqueous phase, as described above, and whose composition is shown in Table III (18.02 g) was added to a 100-mL glass jar. Allyl chloride (2.00 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 6

Liquid aqueous phase, as described above, and whose composition is shown in Table III (13.98 g) was added to a 100-mL glass jar. Allyl chloride (6.02 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 7

Liquid aqueous phase, as described above, and whose composition is shown in Table III (10.07 g) was added to a 100-mL glass jar. Allyl chloride (10.05 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 8

Liquid aqueous phase, as described above, and whose composition is shown in Table III (9.0233 g) was added to a 20-mL sample vial. 1-Chloropropane (1.0083 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 9

Liquid aqueous phase, as described above, and whose composition is shown in Table III (7.0092 g) was added to a 20-mL sample vial. 1-Chloropropane (3.0015 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 10

Liquid aqueous phase, as described above, and whose composition is shown in Table III (5.0046 g) was added to a 20-mL sample vial. 1-Chloropropane (5.0158 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 11

Liquid aqueous phase, as described above, and whose composition is shown in Table III (17.99 g) was added to a 50-mL glass jar. Allyl chloride (2.00 g) was added to the sample vial along with a magnetic stir bar. The mixture was stirred magnetically at a speed sufficient to generate adequate mixing of the two liquid phases (determined visually) at approximately 35° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 12

Liquid aqueous phase, as described above, and whose composition is shown in Table III (14.02 g) was added to a 50-mL glass jar. Allyl Chloride (6.06 g) was added to the sample vial along with a magnetic stir bar. The mixture was stirred magnetically at a speed sufficient to generate adequate mixing of the two liquid phases (determined visually) at approximately 35° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 13

Liquid aqueous phase, as described above, and whose composition is shown in Table III (10.04 g) was added to a 50-mL glass jar. Allyl Chloride (10.01 g) was added to the sample vial along with a magnetic stir bar. The mixture was stirred magnetically at a speed sufficient to generate adequate mixing of the two liquid phases (determined visually) at approximately 35° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 14a

Liquid aqueous phase, as described above, and whose composition is shown in Table III (90.0 g) was added to an 8-oz. glass jar. 1,2-Dichlorobenzene (10.04 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 14b

The liquid aqueous phase resulting from experiment 14a and whose composition is shown in Table III was added to an 8-oz. glass jar. 1,2-Dichlorobenzene (10.02 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 14c

The liquid aqueous phase resulting from experiment 14b and whose composition is shown in Table III was added to an 8-oz. glass jar. 1,2-Dichlorobenzene (10.07 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 14d

The liquid aqueous phase resulting from experiment 14c and whose composition is shown in Table III was added to an 8-oz. glass jar. 1,2-Dichlorobenzene (10.12 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 14e

The liquid aqueous phase resulting from experiment 14d and whose composition is shown in Table III was added to an 8-oz. glass jar. 1,2-Dichlorobenzene (10.00 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 15a

Liquid aqueous phase as described in the text above and whose composition is shown in Table III (90.0 g) was added to an 8-oz. glass jar. Allyl chloride (10.02 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 15b

The liquid aqueous phase resulting from experiment 15a and whose composition is shown in Table III was added to an 8-oz. glass jar. Allyl chloride (10.01 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 15c

The liquid aqueous phase resulting from experiment 15b and whose composition is shown in Table III was added to an 8-oz. glass jar. Allyl chloride (10.06 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 15d

The liquid aqueous phase resulting from experiment 15c and whose composition is shown in Table III was added to an 8-oz. glass jar. 1,2-Dichlorobenzene (10.00 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 15e

The liquid aqueous phase resulting from experiment 15d and whose composition is shown in Table III was added to an 8-oz. glass jar. 1,2-Dichlorobenzene (10.07 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

TABLE III

| Example | Solvent used | aq:solvent (mass ratio) | MeOH | AlC | epi | 1,2-DCB |
|---|---|---|---|---|---|---|
| | Initial aq | | 19.84 | 0.13 | 1.10 | 0.04 |
| 2 | 1,2-DCB | 9:1 | 15.60 | 0.00 | 0.38 | 0.04 |
| 2 | 1,2-DCB | 7:3 | 15.77 | 0.00 | 0.19 | 0.04 |
| 4 | 1,2-DCB | 5:5 | 15.91 | 0.00 | 0.10 | 0.04 |
| 5 | AlC | 9:1 | 15.34 | 0.66 | 0.34 | 0.00 |
| 6 | AlC | 7:3 | 15.67 | 0.64 | 0.14 | 0.00 |
| 7 | AlC | 5:5 | 15.84 | 0.65 | 0.07 | 0.00 |
| 8 | NPC | 9:1 | 15.62 | 0.00 | 0.37 | 0.00 |
| 9 | NPC | 7:3 | 15.87 | 0.00 | 0.15 | 0.00 |
| 10 | NPC | 5:5 | 15.98 | 0.00 | 0.07 | 0.00 |
| 11 | AlC | 9:1 | 15.29 | 0.62 | 0.38 | 0.00 |
| 12 | AlC | 7:3 | 15.48 | 0.75 | 0.15 | 0.00 |
| 13 | AlC | 5:5 | 15.73 | 0.71 | 0.08 | 0.00 |
| 14a | 1,2-DCB | 9:1 | 15.70 | 0.01 | 0.46 | 0.04 |
| 14b | 1,2-DCB | 9:1 | 15.85 | 0.00 | 0.30 | 0.04 |
| 14c | 1,2-DCB | 9:1 | 15.93 | 0.01 | 0.19 | 0.04 |
| 14d | 1,2-DCB | 9:1 | 15.97 | 0.01 | 0.12 | 0.05 |
| 14e | 1,2-DCB | 9:1 | 15.98 | 0.00 | 0.08 | 0.08 |
| 15a | AlC | 9:1 | 15.50 | 0.52 | 0.32 | 0.00 |
| 15b | AlC | 9:1 | 15.62 | 0.57 | 0.15 | 0.00 |
| 15c | AlC | 9:1 | 15.90 | 0.35 | 0.07 | 0.00 |
| 15d | AlC | 9:1 | 15.82 | 0.48 | 0.03 | 0.00 |
| 15e | AlC | 9:1 | 15.85 | 0.48 | 0.01 | 0.00 |

For Table III, "aq"=Liquid Aqueous Phase; "MeOH"=methanol; "AlC"=allyl chloride; "epi"=epichlorohydrin; "1,2-DCB"=1,2-dichlorobenzene; "NPC"=1-chloropropane.

What is claimed:

1. A process for separating phases of a mixture that contain an oxirane, comprising:
   receiving the mixture including a liquid aqueous phase, a liquid organic phase, the oxirane, and a solid phase titanium-silicalite catalyst;
   separating the mixture into the liquid aqueous phase that includes at least water, a peroxide compound, an alcohol and an olefin and the liquid organic phase that includes at least the olefin and a non-reactive co-solvent, where both the liquid aqueous phase and the liquid organic phase include the oxirane and wherein the liquid organic phase has a density greater than the liquid aqueous phase, the solid phase titanium-silicalite catalyst has a density greater than the liquid organic phase, and the solid phase titanium-silicalite catalyst has an affinity for the liquid aqueous phase, and where a first part of the solid phase titanium-silicalite catalyst remains suspended in the liquid aqueous phase and a second part of the solid phase titanium-silicalite catalyst settles through the liquid organic phase to a density driven position;
   recovering the liquid aqueous phase including the first part of the solid phase titanium-silicalite catalyst; and
   extracting at least the oxirane from the liquid aqueous phase with an extraction solvent.

2. The process of claim 1, wherein the solid phase titanium-silicalite catalyst includes a polar group, a charged group or a combination thereof.

3. The process of claim 1, wherein the first part of the solid phase titanium-silicalite catalyst is greater than 50 weight percent, based on a total weight of the solid phase titanium-silicalite catalyst.

4. The process of claim 1, further including recovering the liquid organic phase from a point within a volume of the liquid organic phase.

5. The process of claim 4, wherein the recovered liquid organic phase contains less than 1 weight percent of the solid phase, based on the total weight of the solid phase.

6. The process of claim 1, further including extracting the olefin from the liquid aqueous phase with the extraction solvent.

7. The process of claim 1, wherein the extraction solvent is present in a process for producing the oxirane, the extraction solvent being different than the olefin.

8. The process of claim 1, wherein the extraction solvent does not increase an amount of the olefin in the liquid aqueous phase.

9. The process of claim 1, wherein the extraction solvent is 1,2-dichlorobenzene.

10. The process of claim 1, wherein the oxirane is epichlorohydrin, the olefin is allyl chloride, and the peroxide compound is hydrogen peroxide.

11. A process for preparing an oxirane comprising the steps of:
   (a) reacting an olefin, wherein the olefin is selected from one of (i) an aliphatic olefin or a halogenated substituted aliphatic olefin, (ii) a cycloaliphatic olefin, (iii) an aromatic olefin, (iv) a cycloaromatic olefin, and (v) mixtures thereof; a solid phase titanium-silicalite catalyst, a hydrogen peroxide solution, and a solvent mixture with an alcohol and a non-reactive co-solvent to form a reaction mixture;
   (b) separating an effluent containing the reaction mixture and reaction products into a liquid aqueous phase that includes at least water, the hydrogen peroxide solution, the alcohol and the olefin and a liquid organic phase that includes the olefin and the non-reactive co-solvent, where both the liquid aqueous phase and the liquid organic phase include the oxirane, to separate the solid phase titanium-silicalite catalyst from the liquid organic phase, wherein the liquid organic phase has a density greater than the liquid aqueous phase, the solid phase titanium-silicalite catalyst has a density greater than the liquid organic phase, and the solid phase catalyst has an affinity for the liquid aqueous phase, and wherein a first part of the solid phase catalyst remains suspended in the liquid aqueous phase and a second portion of the solid phase catalyst settles through the liquid organic phase to a density driven position;
   (c) recovering, in at least one operation unit, the liquid organic phase of step (b) including the non-reactive co-solvent, the olefin, and the oxirane;
   (d) recovering, in at least one operation unit, the liquid aqueous phase of step (b) including the first part of the solid phase catalyst; and
   (e) extracting, in at least one separation unit operation, the olefin and oxirane present in the liquid aqueous phase of step (d) from the liquid aqueous phase with an extraction solvent.

12. The process of claim 11, further including the steps:
   (f) separating the oxirane from the liquid organic phase;
   (g) recovering the oxirane from step (f); and
   (h) recycling a remaining amount of the olefin and the solvent mixture with the alcohol and the non-reactive co-solvent stream of step (g) to the reaction mixture.

13. The process of claim 11, wherein the extraction solvent is a solvent present in the process for producing the oxirane, the extraction solvent being different than the olefin.

14. The process of claim 11, wherein the extraction solvent is 1,2-dichlorobenzene.

* * * * *